United States Patent [19]

Toledo-Pereyra

[11] Patent Number: 4,471,629
[45] Date of Patent: Sep. 18, 1984

[54] METHOD OF FREEZING AND TRANSPLANT OF KIDNEYS AND APPARATUS

[75] Inventor: Luis H. Toledo-Pereyra, Grosse Pointe Farms, Mich.

[73] Assignee: Mount Carmel Research and Education Corporation, Detroit, Mich.

[21] Appl. No.: 499,560

[22] Filed: May 31, 1983

[51] Int. Cl.$^3$ .............................................. F17D 17/02
[52] U.S. Cl. ......................................... 62/64; 62/78; 435/1
[58] Field of Search ................ 62/64, 78, 306; 435/1, 435/283

[56] References Cited

U.S. PATENT DOCUMENTS

| | | | |
|---|---|---|---|
| 3,214,937 | 11/1965 | Cannon et al. | 62/384 |
| 3,267,687 | 8/1966 | Manning et al. | 62/168 |
| 3,406,531 | 10/1968 | Swenson et al. | 62/306 |
| 3,450,153 | 6/1969 | Hildebrandt et al. | 137/486 |
| 3,475,918 | 11/1969 | Burton | 62/165 |
| 3,545,221 | 12/1970 | Swenson et al. | 62/231 |
| 3,607,646 | 9/1971 | de Roissart | 62/306 |
| 3,753,865 | 8/1973 | Belzer et al. | 195/127 |
| 3,777,507 | 12/1973 | Burton et al. | 62/306 |
| 3,868,828 | 3/1975 | Schwartz | 62/306 |
| 3,914,954 | 10/1975 | Doerig | 62/306 |
| 3,995,444 | 12/1976 | Clark et al. | 62/306 |
| 4,186,565 | 2/1980 | Toledo-Pereyra | 62/306 |
| 4,242,883 | 1/1981 | Toledo-Pereyra | 62/306 |

OTHER PUBLICATIONS

Journal of Surgical Research 28, pp. 563-570 (1980) "Factors Involved in Successful Freezing of Kidneys for Transplantation", Louis H. Toledo-Pereyra.
Journal of Surgical Research 32, pp. 75-84 (1982) "Organ Freezing", Louis H. Toledo-Pereyra, Debra A. Gordon, and Gerald H. MacKenzie.

*Primary Examiner*—Ronald C. Capossela
*Attorney, Agent, or Firm*—Cullen, Sloman, Cantor, Grauer, Scott & Rutherford

[57] ABSTRACT

In the method of freezing and transplanting a kidney including the successive steps of excising, flushing, hypothermically infusing, freezing, thawing, infusing and implantation, the improvement including the steps of metering and infusing pressurized chilled helium into the renal artery while progressively and rapidly cooling the kidney located on a support of a container that is not immersed but surrounded by a body of liquid nitrogen, while continuously metering nitrogen into the body of liquid nitrogen and simultaneously and continuously recording temperatures and rate for cooling. The kidney is held above the liquid nitrogen by the support and is subjected to the pressurized nitrogen atmosphere within the cooling chamber or tank. A further step in which the thawing includes the application of infrared radiation to the kidney within a confined area while continuously rotating the kidney for uniform thawing. A cryogenic apparatus for controlled freezing of a kidney includes an insulated tank holding a body of liquid nitrogen, with a fitting through the tank adapted for connection to a source of pressurized nitrogen. A coil is immersed within the liquid nitrogen has an inlet fitting which projects outwardly of the tank adapted for connection to a source of pressurized helium and has an outlet adapted for connection to renal artery of the kidney in a container immersed in the liquid nitrogen. A thermocouple within the tank interconnects the kidney with an exterior temperature recorder.

11 Claims, 5 Drawing Figures

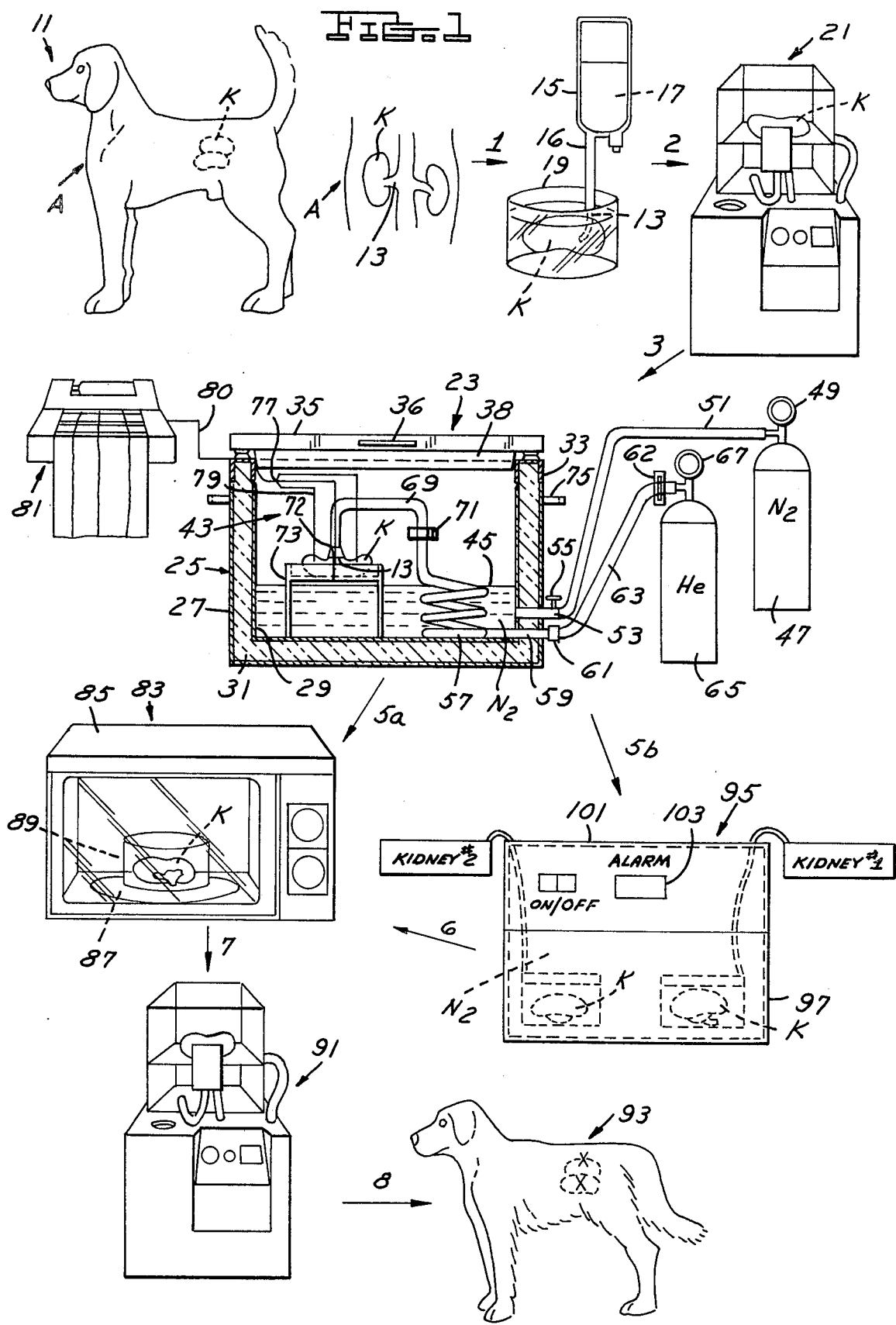

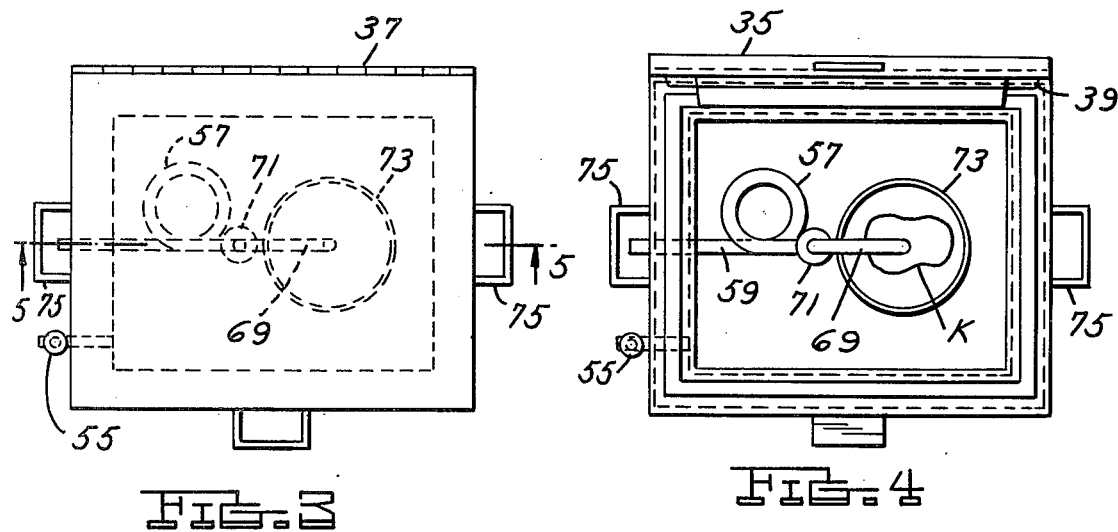
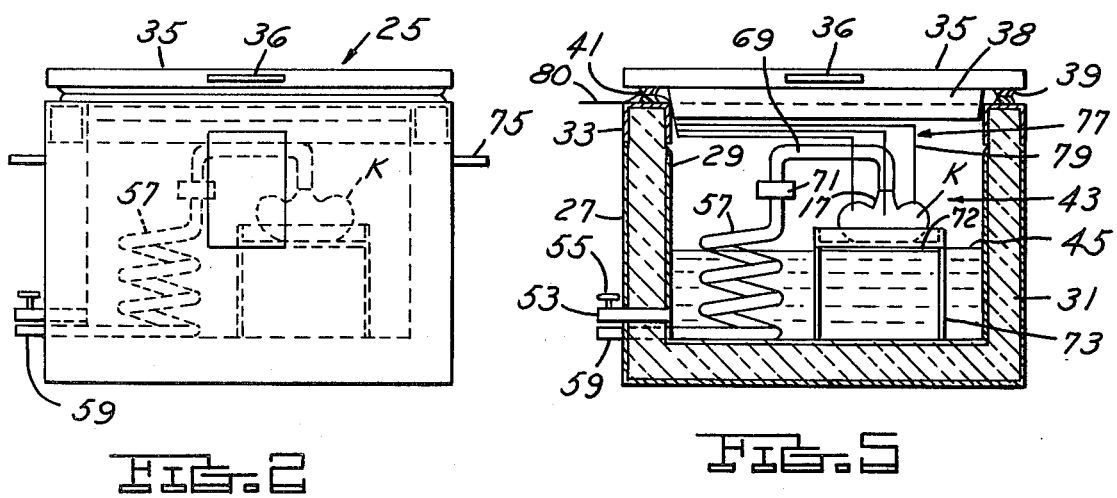

METHOD OF FREEZING AND TRANSPLANT OF KIDNEYS AND APPARATUS

BACKGROUND OF THE INVENTION

For a number of years in the field of transplanting organs from one body to another, efforts have been made to store such organs, particularly kidneys, experimentally with dogs for illustration, and to subsequently transplant the organ into the same or different animal. Heretofore, most attempts undertaken to freeze organs and in particular kidneys, for transplantation have been unsuccessful. Subsequent to excising or removing by surgical procedure a kideny, such as from a dog, there has been an initial step of flushing the kidney with flushing solutions and thereafter subjecting the kidney to perfusion with plasma-like substances and chemicals referred to as cryoprotective agents and thereafter freezing the kidney. Subsequent to freezing for a predetermined interval at a predetermined temperature, the kidney has been thawed within a suitable oven and thereafter subjected to a second hypothermic pulsatile perfusion to remove from the kidney the cryoprotective agent. Thereafter as a final step, the kidney is transplanted into an animal.

To date there has been multiple efforts in this process, most of which have been unsuccessful, or if successful only for a very limited period. Difficulties have been involved in the use of cryoprotective agents employed in conventional hypothermic pulsatile perfusion and the subsequent manner of freezing of the organ.

Problems have arisen as to speed at which freezing should occur and final temperatures to be achieved during flushing, during perfusion and during freezing. Further problems have existed in the manner in which the kidney is frozen in time periods, i.e., rate of cooling, whether it be a slow freeze or a fast freeze and the final temperature at which the kidney is maintained. Further, other problems have arisen in the means by which the kidney is thawed, whether it be in a heating area for fast thawing or slow thawing. Finally, another problem relates to the use of hypothermic pulsatile perfusion upon the thawed kidney to remove the cryogenic protective agents all before transplant into the animal.

Heretofore kidneys after exising are flushed with cold (4° C.) heparinized (10,000 u'liter) Ringer's lactate through the renal artery until the venous effluent was clear. Thereafter, the kidney was treated under hypothermic pulsatile perfusion utilizing plasma-like perfusates and certain liquid protective agents as for example DMSO known as Dimethyl Sulfoxide, or Glycerol. Freezing has been practiced after 6 to 24 hours of perfusion with the kidneys placed in a freezing apparatus by metering helium intraarterially through the renal artery flowing at a rate of 1500 cc count per minute approximately. Heretofore, liquid nitrogen was circulated around the helium line cooling the helium for infusion into the renal artery of the kidney. Also the kidney has been chilled down to −85° C. to −120° C., for illustration, over a predetermined period to five or more minutes and thereafter maintained at said temperature for a period of time.

Various techniques have been applied for thawing the frozen kidney utilizing an oven for rapid thawing.

Problems have arisen with the speed at which the kidney was frozen and the temperature at which it was maintained as well as the speed with which the kideny was thawed in the oven, such as a microwave oven. Subsequently, on thawing, the kideny was introduced into a hypothermic pulsatile perfusion apparatus for removing a protective agent and thereafter reimplanted.

While this general method has been tried over a period of years, most efforts have been unsuccessful. This is believed due to lack of knowledge as to the best mode for protecting the organ by the use of perfusion thereinto of protective fluids, the rate of freezing and the extent of freezing.

Various problems have arisen in the lack of uniform thawing of the frozen kidney or other organ or improper or non-uniform thawing or with the rate of thawing not being finally determined as to whether it should be fast throughout or fast initially and slow subsequently up to room temperature. Most of said kidneys have been unsuccessfully transplated back into animals wherein due to the manner of handling and the methods known, the kidney has not performed at proper serum creatinine levels for normalization thereof.

THE PRIOR ART

The Applicant made a presentation of a work entitled "Factors Involved in Successful Freezing of Kidneys for Transplantation", at an Annual Meeting of the Association for Academic Surgery, Great Gorge, N.J. in Nov. 1979, which paper appeared in the Journal of Surgical Research 28, pages 563 to 570, 1980.

The Applicant also submitted for publication on Apr. 24, 1981 an article entitled "Current Research Review Organ Freezing", which was published in the Journal of Surgical Research 32, pages 75 through 84, 1982.

Both of these articles disclose background of the current method of organ freezing and set forth the parameters involving the multiple steps including nephrectomy, flushing, hypothermic pulsatile perfusion, freezing, thawing, further hypothermic perfusion and subsequent transplant.

These articles are generally definitive of the closest known prior art upon which the present invention represents an improvement as to certain of the steps of the method for accomplishing freezing and transplant of organs and particularly kidneys, at this time limited to animals and particularly dogs.

SUMMARY OF THE INVENTION

An important feature of the present invention is the improvement of the method steps and apparatus in conjunction with freezing and the transplant of kidneys, which generally include the successive steps of excising, flushing, perfusing with a cryoprotectant solution, freezing, thawing and reperfusing to remove the cryoprotectants and implantation.

An important feature of the present invention in connection with the freezing of the kidney is metering and infusing pressurized super cooled helium into the renal artery of the kidney for progressively and rapidly cooling the kidney from the inside out. The kidney is placed on a support located in a tank having a body of confined liquid nitrogen. The kidney is held by the support above the liquid nitrogen but is arranged to underlie a confined pressurized nitrogen atmosphere within the tank. Continuous metering of the nitrogen gas into the nitrogen liquid occurs. Simultaneously and continuously with the infusing process a record is made of the temperatures and rate of cooling as applied to the particular kidney.

As a further feature during freezing the continuously metered helium is filtered for removal of impurities before infusion.

A further feature in accordance with the freezing step provides for the super cooling of helium passing through a coil immersed in a body of liquid nitrogen and metering the helium into the renal artery of the kidney for uniform chilling and freezing with the pressurized helium passing from central portions of the kidney outwardly thereof and subjected to a pressurized nitrogen atmosphere.

A further feature in connection with the recording of temperatures and rate of cooling includes using a thermocouple having probes projected into the kidney and electrically transmitting the temperature signals to the exterior of the cooling chamber to a recorder while continuously pressurizing the cooling chamber in a nitrogen atmosphere.

A further feature includes in connection with the cooling step of using a closed cryogenic tank confining a body of liquid nitrogen, with a helium coil immersed within the nitrogen having a fitting projecting outwardly of the tank and adapted for connection to a source of pressurized helium. The outlet of the coil is adapted for connection to the renal artery of the kidney.

A further feature in the freezing step includes a fitting extending through the wall of a cryogenic tank upon the interior in communication with a body of liquid nitrogen therein and on the exterior thereof connected to a source of pressurized nitrogen.

Another feature contemplates substantially all of the components forming a part of the cryogenic tank used in connection with the freezing step being constructed of stainless steel.

Another feature includes in conjunction with the thawing of the frozen kidney of supporting and rotating the confined kidney within a micro-wave oven with a kidney continuously rotated therein upon a turntable for the uniform application of heat waves thereinto.

A further feature includes in connection with the freezing step, the use of a cryogenic tank having a hinged cover sealing the tank with registering peripheral and continuous flexible magnetic beading in registry for magnetically retaining the cover in sealing engagement with the cryogenic tank for maintaining pressurization of the nitrogen atmosphere therein.

Another feature contemplates the intermediate step after initial steps of hypothermic pulsatile perfusion and freezing, and before thawing, of storing the frozen kidney within a freezer bank at a predetermined continuous temperature including monitoring of the temperature.

The invention includes the further feature of utilizing in connection with the freezing step of a sealed tank and cover for confining a body of liquid nitrogen and for confining a pressurized nitrogen vapor thereover including fittings communicating with the body of nitrogen and adapted for connection to a source of nitrogen exteriorly of the tank. A coil of stainless steel is immersed within the body of nitrogen having an inlet projecting through the tank wall adapted for connection to a source of pressurized helium and having an outlet adapted for connection to the interior central portion of the kidney for perfusing super cold helium thereinto and outwardly thereof. The kidney is retained within a receptical immersed within the liquid nitrogen. There is employed a thermocouple having a plurality of probes projected into the kidney including a lead which projects out from the tank under the cover and which is connected to a temperature recorder for the continuous recording of temperature and rate of cooling providing a record and history for the particularly kidney treated.

These and other features and objects will be seen from the following specification and claims in conjunction with the appended drawings.

THE DRAWINGS

FIG. 1 is a schematic block diagram illustrating the steps of the present method as progressively shown by the arrows 1 through 8 and with the intermediate step of storing designated by the arrow 5b.

FIG. 2 is a side elevational view of the cryogenic tank shown in FIG. 1.

FIG. 3 is a plan view thereof.

FIG. 4 is a similar view with the cover in an open position.

FIG. 5 is a vertical section taken in the direction of arrows 5—5 of FIG. 3.

It will be understood that the above drawings are illustrative of one embodiment including the successive steps of the present method and the apparatus therefore and that other steps and apparatus are contemplated within the scope of the claims hereafter set forth.

DETAILED DESCRIPTION OF THE METHOD AND ONE EMBODIMENT OF THE CRYOGENIC APPARATUS

Referring to the drawings in FIG. 1, there is schematically shown by the arrows 1 through 8 the progressive steps of applicant's method generally designated at 11 as a continuous diagram.

The kidneys for treatment in accordance with the present method are designated at K for the animal A, which in the illustrative embodiment is a dog, though not limited thereto. The present method of freezing and transplanting of a kidney includes the general known successive steps of excising, flushing, perfusing with a cryoprotectant solution, freezing, thawing, reperfusing to remove the protectant solution and implantation. An intermediate step after freezing and before thawing is cold stage at 95 within bank 97, FIG. 1.

The present invention is directed to improvements of some of the steps of the present method and with the use of an improved apparatus as described in detail with particular reference to the cryogenic tank construction 25, FIGS. 1-5.

As an initial step of a conventional nature, there is nephrectomy or incision upon the dog A surgically removing one or a pair of kidneys K, each having a central renal artery 13. This is a conventional step. The second illustration fragmentarily and schematically shows a portion of the animal A, the kidneys K with connective renal artery 13.

After incision, the kidney is removed and connected to the flushing apparatus 15 having a delivery tube 16. Stored in container or apparatus 15, for illustration is cold (4° C.) heparinized (10,000 u'liter) Ringer's lactate which is connected to renal artery 13 of the kidney K located in container 19. The flushing continues until the fluid in container 19 for the kidney is clear.

Arrow 2, FIG. 1, designates a third conventional step, sometimes referred to as hypothermic pulsatile perfusion apparatus 21 and wherein the flushed kidney is connected by its renal artery 13. This is a preliminary conventional step involving perfusing the flushed kidney K with a cryoprotectant solution. In the illustrative embodiment and as commonly used in this hypothermic pulsatile perfusion there is employed a cryoprotective agent, such as DMSO (Dimethyl Sulfoxide) or alternatively glycerol may be employed in solution.

The DMSO is in the nature of a penetrating agent and the infusion is for the purpose of penetrating the flushed kidney K with such perfusion agent or cryoprotectant normally occuring at 4° C., pH 7.4, pulse rate 60/min or alternately 30 minutes at 10° C. at a pressure of 60 mm Hg for a period ranging from 6 to 24 hours.

This conventional step is for protecting the flushed kidney K against toxic osmotic complications with the penetrating agent normally applied at a concentration of 12.5 percent approximately, in the illustrative embodiment, though not limited thereto. The foregoing description of the hypotherimc pulsatile perfusing using the DMSO in a perfusate is conventional and the ingredients can vary as well as the proportions and temperature.

In connection with the successive freezing step designated by the arrow 3, FIG. 1, there is shown the cryogenic freezing apparatus 23, shown in further detail in FIGS. 2 through 5. The apparatus 23 includes housing or tank 25 having inner and outer walls 27, 29 consisting of sheets of stainless steel and with a foam plastic intermediate laminate 31, for illustration.

Over the open edge of the tank 25 there is provided the continuous magentic channel or breaker strip 33. Overlying and snugly engaging the top of the tank is a cover 35 with handle 36 on one side and along its opposite side is pivotally connected to the tank by the piano hinge 37, FIG. 3, of stainless steel.

Depending from the cover 35 upon the interior of the tank 25 is the cover seal 38, and outwardly thereof the peripheral sealing bead 39 having a magentic implant 41 therein by which the cover is tightly closed and sealed over the tank. The cover 35 defines chamber 43 and thereunder in use a body of liquid nitrogen 45 is placed.

Pressurized nitrogen storage tank 47, having pressure gauge 49 includes feed conduit 51 connected to the stainless steel fitting 53 which extends through the tank side wall adjacent its bottom and is in communication with the body of liquid nitrogen 45 therein. Fitting 53 includes metering or cut-off valve 55 for regulating the flow of nitrogen into the body of liquid nitrogen 45.

Immersed within the body of liquid nitrogen 45 is a coil 57 of stainless steel having an intake pipe 59 which projects through the wall of the tank 25 adjacent its bottom and includes a fitting 61 of stainless steel adapted for connection to a source of pressurized helium within helium tank 65. The tank 65 includes pressure gauge 67 and an inlet conduit 63 connected to fitting 61 on the exterior of the cryogenic tank 25.

Fitting 61 is in communication with inlet pipe 59 of the coil 57 which has a filter 71 for removing impurities or impure particles from the helium as the pressurized helium is metered through outlet pipe 69 at its end connected to the renal artery 13 of kidney K.

The kidney K, previously subjected to the hypothermic pulsatile perfusion step of a conventional nature is supported on a horizontal support or plate 72 located adjacent the top of the receptical or container 73. The kidney K and plate 72 are kept outside or above the body of liquid nitrogen 45 and underlie the pressurized nitrogen atmosphere in chamber 43. The super cooled helium is directed through the renal artery 13 of the kidney K for outward migration uniformly for freezing the kidney. The liquid nitrogen 45 surrounds the receptical 73 but does not contact the plate 72 or kidney K.

The nitrogen does not occupy the interior of the receptical 73.

Handles 75 project from opposite ends of the tank or housing 25. During freezing of the perfused kidney K a thermocouple 77 is used having a plurality of probes 79, FIGS. 1 and 5, which project down into spaced portions of the kidney. The lead 80 from the thermocouple 77 extends outwardly of the top of tank 25 under the closed cover 35 and is electronically connected to the temperature recorder 81.

The recorder 81 serves as a monitor to provide readings of temperatures of the kidney K being deep frozen and the rate of cooling to provide permanent records of the history of treatment of the particulate kidney K, its rate of cooling and the temperature to which it is chilled or frozen ranging between $-70$ to $-140$ degrees C.

As is known, it is important that there be a predetermined rate of cooling, preferably a fast rate of cooling such as in the range of 1° C. per minute up to 10° C. per minute or faster as selectively determined depending upon various factors including the size of the kidney and other factors for the end result.

It is known from experimenting that the slow gradual freezing is productive of large ice crystals which are harmful to the kidney tissue. As you increase the rate of cooling the crystals formed are small and less damaging to the kidney. The present freezing step incorporates the use of specific apparatus 23 including the recorder 81 by which there can be effective control of predetermined cooling temperatures and rates of cooling and wherein a history or record can be made of the particular kidney treated for factual compilation. As shown in FIG. 1 upon the conduit 63 adjacent the helium pressurized tank 65, there is a manual flow control 62 for regulating the metering of pressurized helium through the coil 57 and as filtered into the kidney K.

A further conventional step includes the thawing as at arrow 5a, FIG. 1, subsequent to the freezing and wherein the frozen kidney was maintained at a predetermined temperature for a predetermined period, subject to many variables.

In the illustrative embodiment, the thawing apparatus is an AMANA Radarange microwave oven, sold by Raytheon Company and by Sears. Microwave oven 85 may be used to provide for a uniform thawing of the frozen kidney in anticipation of transplant.

It is extremely important that the microwaves are applied uniformly to the kidney. For this purpose, the kidney K within container 89 is mounted upon the power rotated turn table 87 within the thawing oven 83.

In practice the thawing is best performed at a relatively high rate suc as from $-70°$ C. up to $0°$ C. and thereafter at a slower rate. For illustration, there may be thawing from $-70°$ C. up to $14°$ C. in the space of 1.5 to 4.5 minutes, for illustration. Thawing may be faster or slower depending upon factors and conditions including the size of the kidney.

In the illustrative embodiment, the infrared microwave oven 85 operates in the range of 918 MHz to 2450 MHz. Under some conditions for fast thawing and utilizing the turntable 87 for uniform application of heat, thawing or warming from $-196°$ to $0°$ C. may take only a period of 90 seconds with uniform heat application insured by the continuous rotation of the kidney upon turn table 87.

Once the thawing has been accomplished, a further step is the return as designated at arrow 7 in FIG. 1 of the kidney to the hypothermic pulsatile perfusion apparatus 91 which is substantially the same as shown at 21 in FIG. 1. This is for the purpose of reperfusing the kidney to remove the DMSO or other cryoprotectant before transplant as a final step 93 shown at arrow 8 with respect to the animal in the diagram, FIG. 1.

As an intermediate step 95 in the present process schematically shown by the block diagram, FIG. 1, following freezing at 23, the frozen kidney K is tranferred into a storage bank 97 where temperatures are maintained between −80° and a −196° C. The freezing temperature should be less than −76° C.

A characteristic of the storage freezer bank 97 is that the frozen kidney will be maintained at less than −76° C., ideally at −196° C., for illustration. Any suitable cooling medium may be employed for maintaining the freezer bank at a predetermined temperature as for example, liquid nitrogen. The bank 97 includes a maximum temperature control alarm 103 for alerting that there may be a partial failing in maintenance of the uniform freezing temperature. The two kidneys 1 and 2 are stored within the storage tank 97 for illustration.

Since the storage at 95 is an intermediate step following freezing at 23, FIG. 1, when it is desired to use the frozen kidney, it is then returned, as designated at arrow 6 to the thawing oven 83 for thawing as above described. Thereafter the kidney is connected to the hypothermic pulsatile reperfusion machine 91 for removing the DMSO or other cryoprotectant before the final transplantation step 93 at arrow 8 in FIG. 1.

As above described, while essentially the steps as generally defined in FIG. 1 are conventional, the present invention is directed to improvements in some of the steps and by the use of an improved cryogenic freezing apparatus 23 for achieving the results desired.

The present invention provides a means by which some of the steps of the present method may be modified so as to be more effective in accomplishing the end result namely the safe transplant of the kidney into an animal and ultimately to humans.

Primarily, it appears necessary that after use of the required perfusing agent DMSO as a cryoprotectant at predetermined preselected temperatures, an important step and believed to be an advance in the art is the freezing step at 23, FIG. 1 together with simultaneous temperature recording and the rate of cooling within parameters predetermined and wherein specific and improved means are provided for directing pressurized helium as chilled by nitrogen freezing the kidney from the inside out at predetermined temperature levels and at rates to achieve the desired storage or subsequent temperature before thawing.

Heretofore the advantage of uniformily applying heating in the oven 83 has been recognized. Heretofore the container 89 has been manually rotated in limited amounts at predetermined intervals. The present invention contemplates an improvement in that the turntable 87 provides for continuous rotation of the thawing kidney K with a uniform application of heat waves throughout its entire body.

Storage of the frozen kidney K may be at temperatures between −76° and −196° C. It is believed that the best storage temperatures are below −76° C.

In connection with the thawing step designated at 83, FIG. 1, too slow of a thawing is disadvantageous due to the formation of large ice crystals, whereas faster thawing causes the ice crystals formed during thawing to be of smaller dimensions to avoid injury to the tissue. Parameters involving use of the present apparatus and particularly the freezer 23 and oven 83 contemplate rapid uniform freezing and rapid uniform thawing.

Having described my invention, reference should now be had to the following claims:

I claim:

1. In the method of freezing and transplanting a kidney having a renal artery including the successive steps of excising, flushing, hypothermically infusing with a cryoprotectant solution, freezing, thawing, reinfusing to remove the protectant solution and implantation, the improvement which comprises continuously metering and infusing pressurized nitrogen cooled helium into the renal artery for progressively and rapidly cooling the kidney, located on a support within a cooling chamber and located above a body of confined liquid nitrogen contained in the chamber while subjecting the kidney to a confined pressurized nitrogen atmosphere within the chamber, while continuously metering pressurized nitrogen into the nitrogen liquid;

and simultaneously continuously recording temperatures and rate of cooling of the kidney for maintaining a predetermined rate of cooling and kidney temperatures.

2. In the method of claim 1, wherein the helium infusion is at 20 mm Hg at 1500 cc per minute, approximately.

3. In the method of claim 1, the intermediate step of continuously filtering the helium for removal of impurities before infusion.

4. In the method of claim 1, wherein the thawing step includes applying infrared radiation to the kidney within a confined area while continuously rotating the kidney for uniform application of heat thereto and for uniform thawing thereof, at a predetermined rate.

5. In the method of claim 4, the thawing step including a power operated turn table supporting and continuously rotating the confined kidney.

6. In the method of claim 1, the step of continuously recording of rate of cooling and temperatures including inserting thermocouples probes into the kidney, electronically transmitting temperature signals to the exterior of the cooling chamber to a recorder while continuously maintaining pressurization within the cooling chamber.

7. In the method of claim 1, the freezing step including a cooling apparatus having a closed cryogenic tank confining said liquid nitrogen, a helium cooling coil immersed in said nitrogen liquid and having a fitting extending outwardly of said tank adapted for connection to a source of pressurized helium and having an outlet adapted for connection to said kidney, a fitting extending through a wall of the tank adapted for connection to a source of pressurized nitrogen, all said components being of stainless steel.

8. In the method of claim 6, said tank having a hinged cover;
registering peripheral continuous flexible beading upon said cover and tank;
and the further step of magnetically retaining the cover to peripherally overlie and seal said tank maintaining pressurization therein.

9. In the method of claim 1, the intermediate step after initial hypothermic infusion and before thawing of storing the frozen kidney within a freezer bank at a predetermined uniform temperature.

10. In the method of claim 1, said freezing step including a sealed tank and cover, for confining said liquid nitrogen and pressurized nitrogen vapor therein;

a fitting extending through a wall of the tank adjacent its bottom adapted for connection to a source of pressurized nitrogen;

a coil immersed within the liquid nitrogen within said tank;

an inlet fitting on one end of said coil projected through a wall of the tank adapted for connection to a source of pressurized metered helium;

said coil having an outlet pipe adapted for connection to the renal artery of a kidney in a container immersed within said liquid nitrogen;

and a thermocouple including a plurality of probes adapted for projection into the kidney and having a lead wire projecting from the tank between the tank and cover adapted for connection to a temperature recorder.

11. In the method of claim 10, the sealing of said tank and cover including registering peripheral magnetic beading upon the top of said tank and underside of said cover for maintaining the cover closed and sealed over said tank.

* * * * *